United States Patent
Wood

(10) Patent No.: US 9,326,672 B2
(45) Date of Patent: May 3, 2016

(54) CONTROLLING INTENSITY OF LIGHT EMITTED BY A DEVICE

(75) Inventor: Robert J. Wood, Syracuse, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 194 days.

(21) Appl. No.: 13/298,323

(22) Filed: Nov. 17, 2011

(65) Prior Publication Data

US 2012/0157776 A1   Jun. 21, 2012

Related U.S. Application Data

(60) Provisional application No. 61/424,704, filed on Dec. 20, 2010.

(51) Int. Cl.

| | | |
|---|---|---|
| *A61B 1/267* | (2006.01) | |
| *A61B 3/00* | (2006.01) | |
| *A61B 1/00* | (2006.01) | |
| *H05B 37/02* | (2006.01) | |
| *A61B 1/227* | (2006.01) | |
| *A61B 1/06* | (2006.01) | |

(52) U.S. Cl.
CPC ........... *A61B 3/0008* (2013.01); *A61B 1/00039* (2013.01); *A61B 1/00066* (2013.01); *A61B 3/0033* (2013.01); *H05B 37/0227* (2013.01); *A61B 1/0661* (2013.01); *A61B 1/227* (2013.01)

(58) Field of Classification Search
CPC ................... A61B 1/00–1/2736; G06F 3/044; F21V 23/00–23/06
USPC .......................... 600/178–180, 185, 199–200; 345/173–184; 362/295
See application file for complete search history.

(56) References Cited

U.S. PATENT DOCUMENTS

| | | | |
|---|---|---|---|
| 4,442,474 A | | 4/1984 | de Jong et al. |
| 4,643,171 A | * | 2/1987 | Riester .......................... 600/200 |
| 6,319,199 B1 | * | 11/2001 | Sheehan et al. ................ 600/200 |
| 6,559,831 B1 | | 5/2003 | Armstrong |
| 6,608,617 B2 | | 8/2003 | Hoffknecht et al. |
| 7,054,133 B2 | | 5/2006 | Orth |
| 7,148,704 B2 | | 12/2006 | Philipp |
| 7,446,429 B2 | | 11/2008 | Togura et al. |
| 7,540,625 B2 | | 6/2009 | Matthews et al. |
| 7,566,996 B2 | | 7/2009 | Altonen et al. |
| 7,834,856 B2 | | 11/2010 | Grinshpoon et al. |
| 2002/0038076 A1 | * | 3/2002 | Sheehan et al. ................ 600/200 |

(Continued)

FOREIGN PATENT DOCUMENTS

| | | |
|---|---|---|
| DE | 19917091 | 6/2000 |
| EP | 1936480 | 6/2008 |

OTHER PUBLICATIONS

Baxter, Larry K.: Capacitive Sensors; © Jun. 26, 2000; Revised Jul. 20, 2000; accessed via: http://www.capsense.com/capsense-wp.pdf; 17 pgs.

(Continued)

*Primary Examiner* — Jan Christopher Merene
*Assistant Examiner* — Steven Cotroneo
(74) *Attorney, Agent, or Firm* — Merchant & Gould P.C.

(57) ABSTRACT

A device has a capacitive surface and a light source. A user of the device uses the capacitive surface to change the intensity of light emitted by the light source. To increase and decrease the intensity of the light emitted by the light source, the user touches the capacitive surface with one or more fingers.

8 Claims, 5 Drawing Sheets

(56) References Cited

U.S. PATENT DOCUMENTS

| | | | |
|---|---|---|---|
| 2003/0171655 A1* | 9/2003 | Newman et al. | 600/200 |
| 2004/0186352 A1* | 9/2004 | Roberts et al. | 600/200 |
| 2005/0052427 A1 | 3/2005 | Wu et al. | |
| 2006/0055679 A1* | 3/2006 | Grinshpoon et al. | 345/173 |
| 2009/0112067 A1* | 4/2009 | Baker | 600/199 |
| 2009/0153495 A1* | 6/2009 | Chen et al. | 345/173 |
| 2009/0231167 A1 | 9/2009 | Chen | |
| 2011/0166421 A1* | 7/2011 | Katiraei | 600/200 |
| 2011/0301425 A1* | 12/2011 | Boukhny et al. | 600/249 |

OTHER PUBLICATIONS

International Search Report and Written Opinion in Application No. PCT/US2011/061105, mailed Jun. 29, 2012, 9 pages.

\* cited by examiner

CONTROLLING INTENSITY OF LIGHT EMITTED BY A DEVICE

RELATED APPLICATION

This application claims the benefit of U.S. Patent Application Ser. No. 61/424,704 on Dec. 20, 2010, the entirety of which is hereby incorporated by reference.

BACKGROUND

Healthcare providers, such as doctors and nurses, frequently use handheld devices when providing healthcare. Many of these handheld devices output light. For example, a healthcare provider can use a handheld otoscope to examine a patient's ear canals. In this example, the otoscope can include a light source for illuminating the patient's ear canals. In another example, a handheld surgical tool can include a light source for illuminating an interior cavity of a patient's body during laparoscopic surgery.

In some circumstances, a healthcare provider may need to adjust the intensity of the light emitted by such handheld devices during use. For example, if a handheld device is emitting too much light, an image produced by the handheld device can appear washed out. Likewise, if a handheld device is emitting too little light, an image produced by the handheld device may be too dark. Hence, as a result of the handheld device emitting too much or too little light, the healthcare provider may not be able to easily see details in the image provided by the handheld device.

Typically, healthcare providers use movable controls on handheld instruments to adjust the intensity of the light emitted by such handheld devices during use. For example, a handheld device can include an analog switch for controlling the intensity of the light emitted by the handheld device. In this example, as a healthcare provider moves the switch in one direction, the handheld device emits more light. As the healthcare provider moves the switch in the opposite direction, the handheld device emits less light. In another example, a handheld device can include a wheel or dial. In this example, as a healthcare provider turns the wheel or dial in one direction, the handheld device emits more light. In this example, the handheld device emits less light as the healthcare provider turns the wheel or dial in the opposite direction.

There can be several drawbacks to using movable controls to adjust the intensity of the light emitted by such handheld instruments. For example, in a healthcare setting, such movable controls can harbor bacteria or permit the entry of fluids into interior areas of the handheld instruments. In another example, movable controls can wear out before other components of handheld devices because foreign objects can become lodged in the movable controls or because of friction within the moving parts of the movable controls.

SUMMARY

A handheld device has a capacitive surface and a light source. A user of the handheld device uses the capacitive surface to control the intensity of light emitted by the light source. To increase the intensity of the light emitted by the light source, the user touches the capacitive surface with a finger and then increases the finger's pressure on the capacitive surface. To decrease the intensity of the light emitted by the light source, the user touches the capacity surface with a finger and then decreases the finger's pressure on the capacitive surface.

In this way, the user can adjust an intensity of light emitted by the handheld device using the capacitive surface instead of using a moving control. Because the capacitive surface is not a moving control, the capacitive surface can be sealed to prevent objects or fluids from entering the handheld device. Furthermore, because the capacitive surface is not a moving control, it may be easier to keep the handheld device clean.

This summary is provided to introduce a selection of concepts. These concepts are further described below in the Detailed Description. This summary is not intended to identify key features or essential features of the claimed subject matter, nor is this summary intended as an aid in determining the scope of the claimed subject matter.

DETAILED DESCRIPTION

Figure 1:
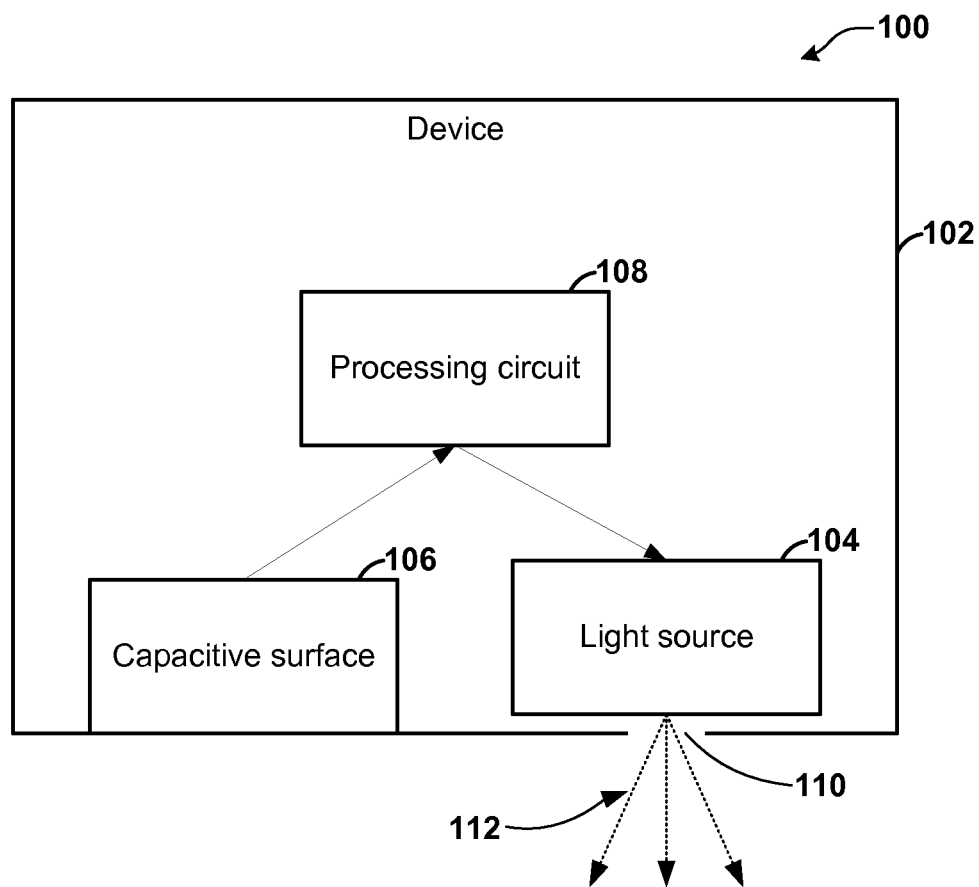
FIG. 1 is a block diagram illustrating example details of a handheld device.

FIG. 1 is a block diagram illustrating example details of a device 100. In various embodiments, the device 100 can be various types of devices. For example, the device 100 can be a handheld otoscope, a retinoscope, an opthalmoscope, a rhinolaryngoscope, a laryngoscope, or another type of healthcare handheld device. In another example, the device 100 can be a non-healthcare handheld device, such as a flashlight. Other embodiments are not necessarily handheld. For example, embodiments can control intensity of light emitted by car headlights.

As illustrated in the example of FIG. 1, the device 100 comprises a housing 102, a light source 104, a capacitive surface 106, and a processing circuit 108. It should be appreciated that the device 100 can include components in addition to the housing 102, the light source 104, the capacitive surface 106 and the processing circuit 108. For example, the device 100 can include a battery, internal wiring, an on/off switch, and/or other components. Such additional components are omitted from the example of FIG. 1 for the sake of clarity.

The housing 102 encloses internal components of the device 100. For example, the housing 102 can enclose the light source 104, the capacitive surface 106, and the processing circuit 108. In various embodiments, the housing 102 can be shaped in various ways. For example, the housing 102 can be shaped to form a handle. The housing 102 can be made of one or more types of materials. For example, the housing 102 can be made of plastic, metal, ceramic, and/or other types of materials. Furthermore, in some embodiments, the device 100 can comprise multiple connected housings that enclose different internal components of the device 100. For example, one of the housings can enclose the light source 104 and another one of the housings can enclose the capacitive surface 106.

The light source 104 is an assembly that emits light. An aperture 110 defined by the housing 102 allows light 112 emitted by the light source 104 to escape from the housing 102. The light source 104 is dimmable. In other words, the intensity of the light 112 emitted by the light source 104 can vary. In various embodiments, the light source 104 can include various types of lamps. For example, the light source 104 can include a halogen lamp, a Light-Emitting Diode (LED) lamp, an incandescent lamp, or another type of dimmable lamp.

Furthermore, the device 100 comprises a capacitive surface 106. The capacitive surface 106 is an assembly that is able to detect changes in capacitance due to proximity of a human finger. In this patent document, the term "finger" refers to both fingers and thumbs. The capacitive surface 106 is positioned within the housing 102 such that the capacitive surface 106 is able to detect changes in capacitance due to proximity of a finger of a user of the device 100. In some embodiments, the capacitive surface 106 is able to detect changes in capacitance due to proximity of the user's finger even when the user is wearing gloves.

While the user is touching the capacitive surface 106, the user can increase the pressure of the user's finger on the capacitive surface 106 over time. As the user increases the pressure of the user's finger on the capacitive surface 106, the surface area of the capacitive surface 106 in contact with the user's finger increases. The surface area of the capacitive surface 106 in contact with the user's finger increases because the user's fingertip tends to increasingly spread out over the capacitive surface 106 as the user increases the pressure of the user's finger on the capacitive surface 106. As the surface area of the capacitive surface 106 that is in contact with the user's finger increases over time, the capacitance of the capacitive surface 106 increases over time.

Furthermore, while the user is touching the capacitive surface 106, the user can decrease the pressure of the user's finger on the capacitive surface 106 over time. As the user decreases the pressure of the user's finger on the capacitive surface 106, the surface area of the capacitive surface 106 in contact with the user's finger decreases. The surface area of the capacitive surface 106 in contact with the user's finger decreases because the user's fingertip becomes less spread out on the capacitive surface 106 as the user decreases the pressure of the user's finger on the capacitive surface 106. As the surface area of the capacitive surface 106 that is in contact with the user's finger decreases over time, the capacitance of the capacitive surface 106 decreases over time.

In various embodiments, the capacitive surface 106 can have various sizes. For example, in some embodiments, the capacitive surface 106 can be slightly larger than an average-sized last phalange of a human finger. In other embodiments, the capacitive surface 106 is smaller than an average-sized last phalange of a human finger. For example, the capacitive surface 106 can be a 1 cm square.

The capacitive surface 106 outputs a signal to the processing circuit 108. The signal encodes the capacitance of the capacitive surface 106. As described below with reference to FIG. 2, the processing circuit 108 controls the intensity of the light 112 emitted by the light source 104 based on whether the capacitance of the capacitive surface 106 increases or decreases over time. Thus by increasing or decreasing the pressure of the user's finger on the capacitive surface 106 after initially touching the capacitive surface 106, the user can use the capacitive surface 106 to change the intensity of the light 112 emitted by the light source 104. Consequently, the device 100 does not need to include moving parts in order to enable the user to change the intensity of the light 112 emitted by the light source 104. Furthermore, the device 100 enables the user to change (i.e., increase or decrease) the intensity of the light 112 without the user translating (e.g., sliding) the user's finger on the capacitive surface. In addition, the device 100 enables the user to control the intensity of the light 112 without bending, deflecting, or otherwise moving the capacitive surface 106.

In various embodiments, the processing circuit 108 can be implemented in various ways. For example, the processing circuit 108 can comprise one or more Application-Specific Integrated Circuits (ASICs). In another example, the processing circuit 108 can comprise one or more integrated circuits that execute computer-executable instructions.

Figure 2:
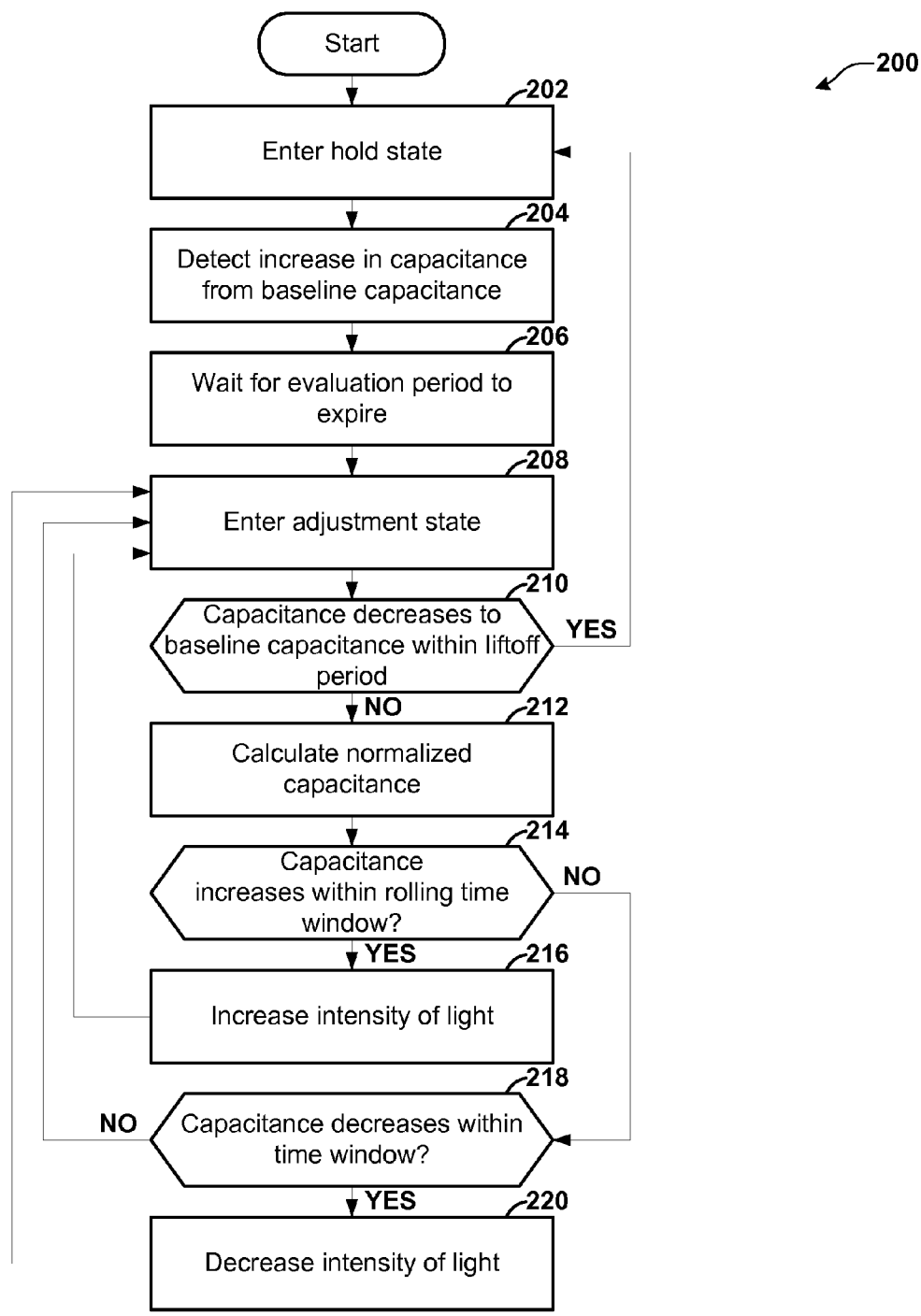
FIG. 2 is a flowchart illustrating an example operation of a processing circuit.

FIG. 2 is a flowchart illustrating an example operation 200 of the processing circuit 108. It should be appreciated that the operation 200 is an example. In other embodiments, the processing circuit 108 can perform other operations. For example, in other embodiments, the processing circuit 108 can perform operations with more or fewer steps. In yet other embodiments, the processing circuit 108 can perform the steps of the operation 200 in different orders.

When the device 100 is powered on, the processing circuit 108 enters a hold state (202). While the processing circuit 108 is in the hold state, the processing circuit 108 does not cause the light source 104 to change the intensity of the light 112 emitted by the light source 104.

As previously mentioned, the processing circuit 108 receives a signal from the capacitive surface 106. The signal represents a capacitance of the capacitive surface 106. In some embodiments, the signal from the capacitive surface 106 is an analog signal. In embodiments where the signal is an analog signal, the processing circuit 108 can convert the analog signal into a digital signal comprising a series of samples. The samples indicate capacitances of the capacitive surface 106 at different points in time. In other embodiments, the signal received from the capacitive surface 106 is a digital signal comprising a series of samples indicating capacitances of the capacitive surface 106 at different points in time. When the user's finger is not touching the capacitive surface 106, the capacitance of the capacitive surface 106 is at a baseline level. The processing circuit 108 monitors the signal from the capacitive surface 106 while the processing circuit 108 is in the hold state.

When the processing circuit 108 is in the hold state, the processing circuit 108 can detect an increase in the capacitance from the baseline level (204). This increase in the capacitance from the baseline level can coincide with the user's finger touching the capacitive surface 106.

When the processing circuit 108 detects such an increase in the capacitance from the baseline level, the processing circuit 108 waits for an evaluation period to expire (206). The processing circuit 108 continues to monitor the signal from the capacitive surface 106 while the processing circuit 108 is waiting for the evaluation period to expire.

After the evaluation period expires, the processing circuit 108 enters an adjustment state (208). The processing circuit 108 continues to monitor the signal from the capacitive surface 106 while the processing circuit 108 is in the adjustment state.

While the processing circuit 108 is in the adjustment state, the processing circuit 108 detects whether the capacitance has dropped back to the baseline level within a liftoff period (210). The liftoff period is approximately equal in duration to an amount of time required for the user to lift the user's finger completely off the capacitive surface. If the capacitance has dropped back to the baseline level within the liftoff period ("YES" of 210), the processing circuit 108 re-enters the hold state (202). After the processing circuit 108 re-enters the hold state, the processing circuit 108 can repeat the operation 200. For instance, if after performing the operation 200, the processing circuit 108 has caused the light source 104 to increase the intensity of the light 112 to a first level, the processing circuit 108 can repeat the operation 200 again so that the intensity of the light 112 increases from the first level to a second level. Consequently, if the user's finger lifts off the capacitive surface 106 when the intensity of the light 112 reaches a certain level, and the user can continue to increase the intensity of the light 112 by touching the capacitive surface 106 again and increasing the pressure on the capacitive surface 106.

If the capacitance has not dropped back to the baseline level within the liftoff period ("NO" of 210), the processing circuit 108 calculates a normalized capacitance of the capacitive surface 106 at an end of a rolling time window that ends at the current time (212). In some embodiments, the rolling time window can be equal in duration to the evaluation period discussed above. The processing circuit 108 waits for the evaluation period in order to sample capacitances of the capacitive surface 106 occurring after the rise in capacitance from the baseline level coinciding with the user's finger initially touching the capacitive surface 106. The capacitances of the capacitive surface 106 occurring during the rise in capacitance from the baseline level are not necessarily indicative of whether the user wants to increase or decrease the intensity of the light 112.

In various embodiments, the processing circuit 108 calculates the normalized capacitance in various ways. For example, the processing circuit 108 can calculate the normalized capacitance as a mean of the capacitances sampled during the rolling time window. In another example, the processing circuit 108 can calculate the normalized capacitance as a median of the capacitances sampled during the rolling time window. In yet another example, the processing circuit 108 can calculate the normalized capacitance as the last capacitance sampled during the rolling time window. In yet another example, the processing circuit 108 can calculate the normalized capacitance as the integral of the capacitances sampled during the rolling time window. Calculating the normalized capacitance in these ways can, in some embodiments, smooth out changes in capacitance caused by uneven pressure of the user's finger on the capacitive surface 106.

After calculating the normalized capacitance of the capacitive surface 106 at the end of the rolling time window, the processing circuit 108 determines whether the normalized capacitance has increased during the rolling time window (214). If the normalized capacitance has increased during the rolling time window ("YES" of 214), the processing circuit 108 causes the light source 104 to increase the intensity of the light 112 (216). After increasing the intensity of the light 112, the processing circuit 108 again enters the adjustment state (208). After re-entering the adjustment state, the processing circuit 108 can continue to adjust the intensity of the light 112 based on the capacitance of the capacitive surface 106.

On the other hand, if the normalized capacitance has not increased during the rolling time window ("NO" of 214), the processing circuit 108 determines whether the normalized capacitance has decreased during the rolling time window (218). If the normalized capacitance has decreased during the rolling time window ("YES" of 218), the processing circuit 108 causes the light source 104 to decrease the intensity of the light 112 (220). After decreasing the intensity of the light 112, the processing circuit 108 again enters the adjustment state (208). After re-entering the adjustment state, the processing circuit 108 can continue to adjust the intensity of the light 112 based on the capacitance of the capacitive surface 106. Because the processing circuit 108 re-enters the adjustment state and because the capacitance can increase without the user lifting the user's finger off the capacitive surface, the processing circuit 108 can, in some embodiments, cause the light source 104 to increase and also decrease the intensity of the light 112 without the user lifting the user's finger off the capacitive surface 106.

In various embodiments, the processing circuit 108 can determine whether the normalized capacitance has increased or decreased during the rolling time window in various ways. For example, the processing circuit 108 can determine that the normalized capacitance has increased or decreased during the rolling time window when the normalized capacitance is greater or less than a normalized capacitance at the beginning of the rolling time window.

Furthermore, in various embodiments, the processing circuit 108 can cause the light source 104 to increase or decrease the intensity of the light 112 by various amounts. For example, if the normalized capacitance has increased or decreased during the rolling time window, the processing circuit 108 can cause the light source 104 to increase or decrease the intensity of the light 112 by a fixed amount. In another example, the processing circuit 108 can cause the light source 104 to increase or decrease the intensity of the light 112 by an amount related to an amount by which the normalized capacitance increased or decreased during the rolling time window. For instance, in this example, the processing circuit 108 can cause the light source 104 to increase or decrease the intensity of the light 112 by an amount directly proportional to an amount by which the normalized capacitance increased or decreased during the rolling time window.

Figure 3:
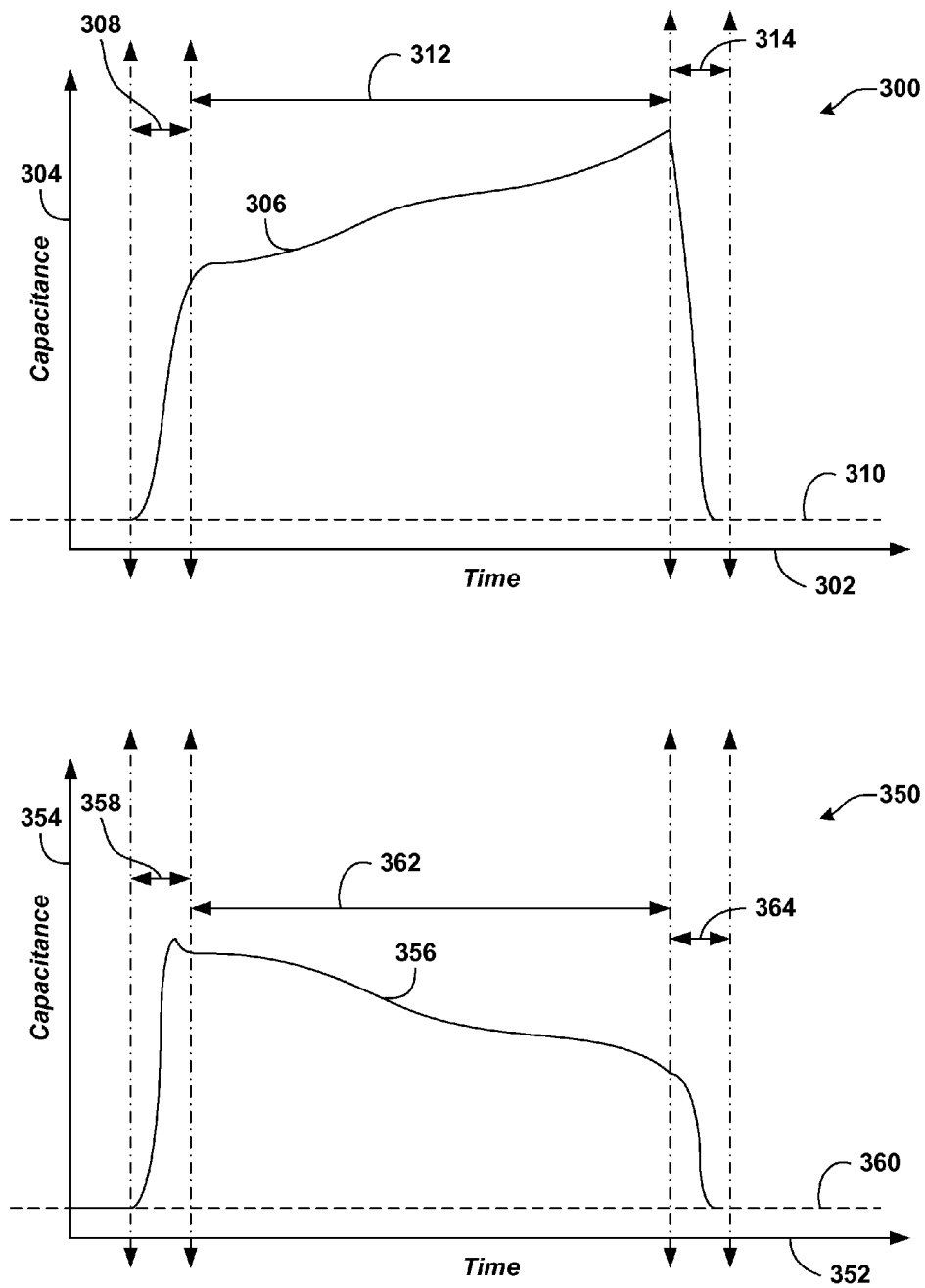
FIG. 3 illustrates charts showing capacitance of a capacitive surface over time.

FIG. 3 illustrates charts showing capacitance of the capacitive surface 106 over time. The example of FIG. 3 includes a first chart 300 and a second chart 350. The first chart 300 has a time axis 302 and a capacitance axis 304. Points that are further to the right on the time axis 302 correspond to later times. Points that are higher on the capacitance axis 304 correspond to higher capacitances of the capacitive surface 106.

A capacitance curve 306 is plotted in the first chart 300 on the time axis 302 and the capacitance axis 304. In an onset time interval 308, the capacitance curve 306 rises sharply from a baseline level 310. The rising capacitance during the onset time interval 308 can correspond to the user's finger initially touching the capacitive surface 106. The processing circuit 108 does not cause the light source 104 to increase or decrease the intensity of the light 112 during the onset time interval 308.

In an adjustment time interval 312, the capacitance curve 306 gradually increases over time. The rising capacitance during the adjustment time interval 312 can correspond to the user's finger pressing harder onto the capacitive surface 106. During the adjustment time interval 312, the processing circuit 108 can cause the light source 104 to increase the intensity of the light 112.

In a liftoff time interval 314, the capacitance curve 306 falls sharply back to the baseline level 310. The duration of the liftoff time interval 314 can be equal to the duration of the liftoff period discussed above. The falling capacitance during the liftoff time interval 314 can correspond to the user's finger lifting off the capacitive surface 106.

Like the first chart 300, the second chart 350 has a time axis 352 and a capacitance axis 354. Points that are further to the right on the time axis 352 correspond to later times. Points higher on the capacitance axis 354 correspond to higher capacitances of the capacitive surface 106.

A capacitance curve 356 is plotted in the second chart 350 on the time axis 352 and the capacitance axis 354. In an onset time interval 358, the capacitance curve 356 rises sharply from a baseline level 360. The rising capacitance during the onset time interface 358 can correspond to the user's finger initially touching the capacitive surface 106. The processing circuit 108 does not cause the light source 104 to increase or decrease the intensity of the light 112 during the onset time interval 358.

In an adjustment time interval 362, the capacitance curve 356 gradually decreases over time. The decreasing capacitance during the adjustment time interval 362 can correspond to the user's finger pressing less hard onto the capacitive surface 106. During the adjustment time interval 312, the processing circuit 108 can cause the light source 104 to decrease the intensity of the light 112.

In a liftoff time interval 364, the capacitance curve 306 falls sharply back to the baseline level 360. The duration of the liftoff time interval 364 can be equal to the duration of the liftoff period. The falling capacitance during the liftoff time interval 364 can correspond to the user's finger lifting off the capacitive surface 106.

The capacitances and times shown in the charts 300 and 350 merely serve to show the general shapes of capacitance curves over time. The charts 300 and 350 in the example of FIG. 3 are not intended to express real capacitances or real relationships of capacitances over time.

Figure 4:
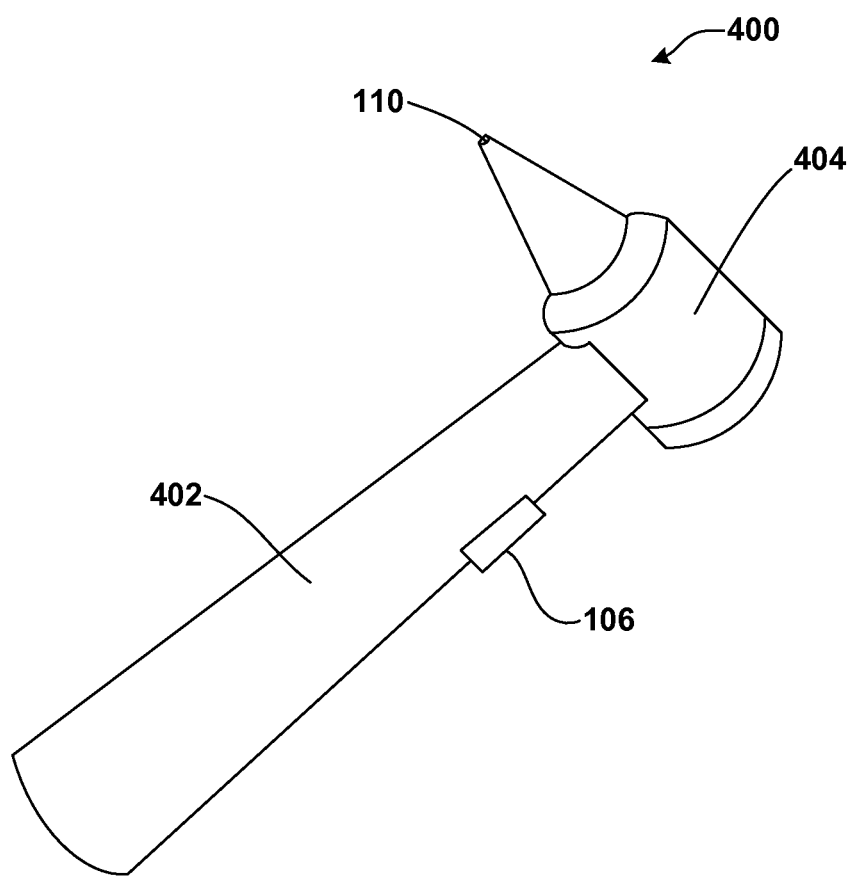
FIG. 4 illustrates an example handheld otoscope.

FIG. 4 illustrates an example handheld otoscope 400. The handheld otoscope 400 is an example embodiment of the device 100. Although the example of FIG. 4 illustrates a handheld otoscope, it should be appreciated that the device 100 can be devices other than handheld otoscopes.

In the example of FIG. 4, the handheld otoscope 400 includes a handle 402 and a head 404. A user can hold the handheld otoscope 400 by wrapping the user's fingers around the handle 402. The handle 402 can contain a power source (e.g., batteries) and the processing circuit 108 (not shown). The head 404 includes the light source 104 (not shown). Light escapes from the head 404 through the aperture 110.

Furthermore, the capacitive surface 106 is disposed on the handle 402 of the handheld otoscope 400. In the example of FIG. 4, the capacitive surface 106 is disposed on the handle 402 such that the user may be able to use the user's thumb to control the intensity of the light emitted by the handheld otoscope 400. In the example of FIG. 4, the capacitive surface 106 extends from the handle 402. In other embodiments, the capacitive surface 106 can be flush with the surface of the handle 402. Furthermore, in some embodiments, the capacitive surface 106 is on the head 404 instead of on the handle 402.

Figure 5:
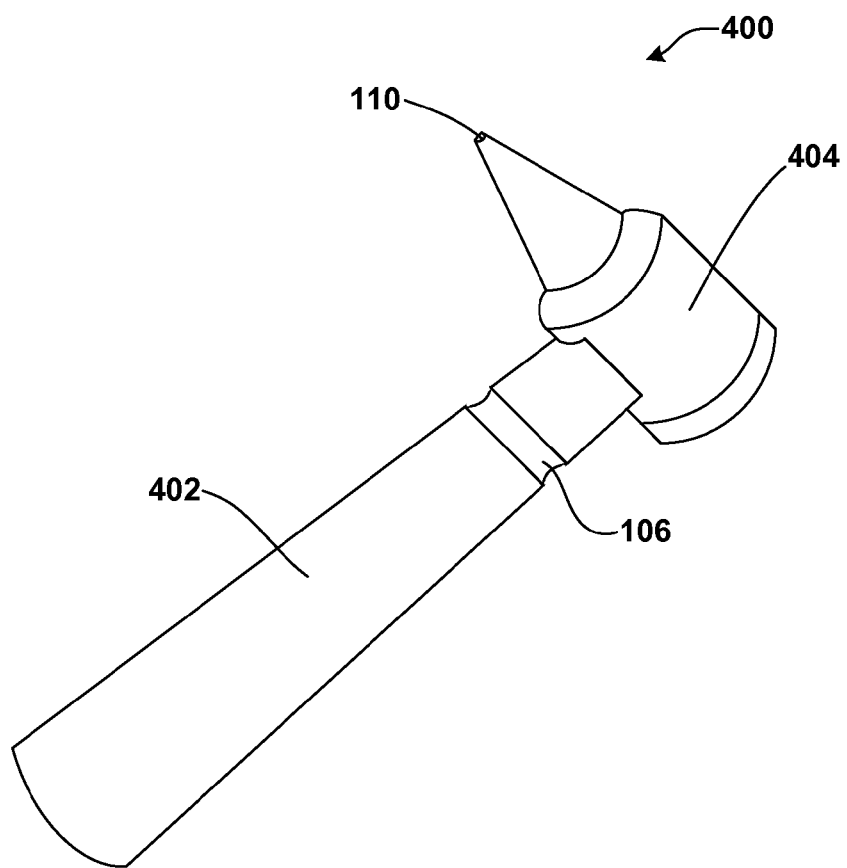
FIG. 5 illustrates another example handheld otoscope.

Referring now to FIG. 5, another example handheld otoscope 500 is shown. The handheld otoscope 500 is similar to the handheld otoscope 400 described above.

However, the capacitive surface 106 on the handheld otoscope 500 surrounds at least a portion of the handle 402. In this example, the capacitive surface 106 extends 360 degrees around the handle 402 so that the capacitive surface 106 is accessible at any orientation of the handheld otoscope 500.

In addition, in one example, the handheld otoscope 500 is programmed to automatically start at full brightness/intensity when grasped by a user. When any portion of the capacitive surface 106 is touched, the handheld otoscope 500 begins to dim at a controlled rate. When the user removes his/her touch from the capacitive surface 106, the handheld otoscope 500 will remain at the current light intensity.

If the capacitive surface 106 is then touched again, the intensity reverses, becoming increasingly intense until the touch is removed. When removed, the handheld otoscope 500 will remain at the selected intensity. Upon each re-touch of the capacitive surface 106, the light intensity will continually reverse between increasing and decreasing, thereby allowing the user ease in control.

In some embodiments, the capacitive surface 106 can be configured as a single sense pad extending around the periphery of the handle 402. The handheld otoscope 500 includes logic to sense a number of fingers touching the capacitive surface 106. This can be accomplished by measuring the capacitive field strength created by the touch. The greater the number of fingers touching the capacitive surface 106, the greater the capacitive field strength that is generated.

When two fingers are touching the capacitive surface 106, the intensity of the light can be increased incrementally at a greater amount. More fingers further increase the intensity. Fewer fingers decrease the intensity. In this manner, the user can control the intensity of the light by increasing or decreasing the number of fingers that touch the capacitive surface 106.

In other examples, different touch scenarios can be used to control the handheld otoscope 500. For example, a multi-finger touch can instead be used to set the intensity of the light at a specific amount, or can be used to reset the intensity. In another example, multiple touch points can be used, and the user can increase or decrease intensity by touching the multiple touch points in particular patterns. For example, the intensity can increase if the user touches two specific touch points. Likewise, the intensity can decrease if the user touches two different touch points. Other configurations are possible.

The various embodiments described above are provided by way of illustration only and should not be construed as limiting. Those skilled in the art will readily recognize various modifications and changes that may be made without following the example embodiments and applications illustrated and described herein.

What is claimed is:

1. A medical device comprising:
    a medical instrument;
    a handle;
    a capacitive surface disposed on the handle;
    a head, including a light source that emits light, an intensity of the light changing in response to a user's finger touching the capacitive surface; and
    a processing circuit that receives a signal that encodes a capacitance of the capacitive surface, the processing circuit causing the light source to change the intensity of the light based on changes to capacitance of the capacitive surface after the user's finger initially touches the capacitive surface, and wherein the processing circuit causes the light source to increase the intensity of the light and also decrease the intensity of the light without the user lifting the user's finger off the capacitive surface, wherein upon detecting a capacitance exceeding a baseline level of the capacitive surface prior to the user's finger initially touching the capacitive surface, the processing circuit:
        calculates a normalized capacitance for a rolling time window using at least two samples, the at least two samples representing capacitances of the capacitive surface at least two times during the rolling time window;
        causes the light source to increase the intensity of the light when the normalized capacitance has increased during the rolling time window; and
        causes the light source to decrease the intensity of the light when the normalized capacitance has decreased during the rolling time window.

2. The device of claim 1, wherein the intensity decreases upon the user's finger touching the capacitive surface until the user's finger releases the capacitive surface.

3. The device of claim 1, wherein the intensity increases upon a greater number of the user's fingers touching the capacitive surface.

4. The device of claim 1, wherein the intensity decreases upon a lesser number of the user's fingers touching the capacitive surface.

5. The device of claim 1, wherein the intensity of the light increases in response to a pressure of the user's finger on the capacitive surface increasing after the user's finger initially touches the capacitive surface, and wherein the intensity of the light decreases in response to a pressure of the user's finger on the capacitive surface decreasing after the user's finger initially touches the capacitive surface.

6. The device of claim 1, wherein no moving parts are involved when changing the intensity of the light.

7. The device of claim 1, wherein the processing circuit calculates the normalized capacitance as a mean of the capacitances represented by the samples.

8. The device of claim 1, wherein the processing circuit causes the light source to increase the intensity of the light by an amount directly related to an amount by which the capacitance increased during the rolling time window; and wherein the processing circuit causes the light source to decrease the intensity of the light by an amount directly related to an amount by which the capacitance decreased during the rolling time window.

* * * * *